Figure 4:
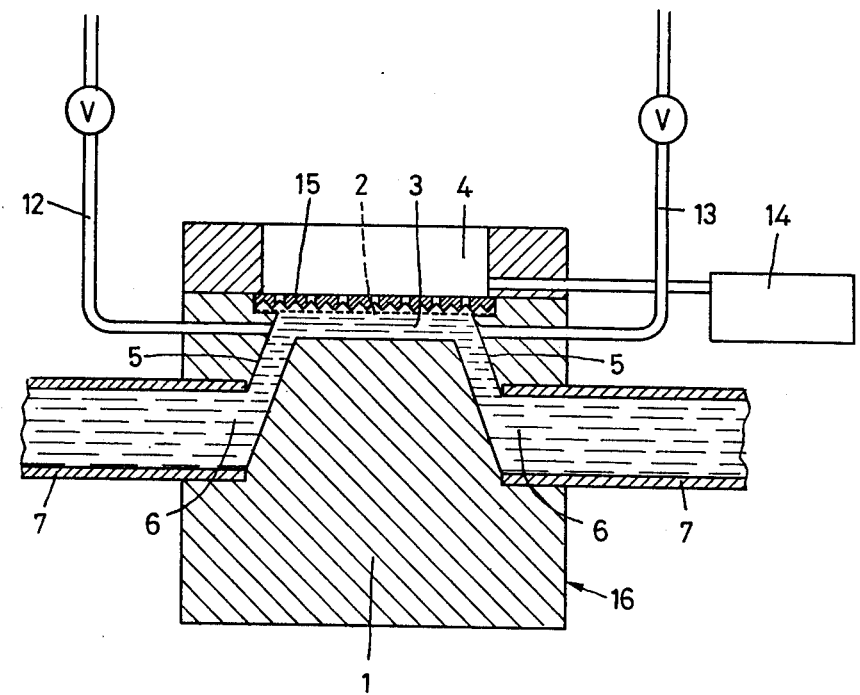

United States Patent [19]

Trechsel

[11] 4,001,117
[45] Jan. 4, 1977

[54] SIEVE FILTRATION APPARATUS
[75] Inventor: Ulrich Trechsel, Bern, Switzerland
[73] Assignee: Pathophysiologisches Institut der Universitat Bern, Bern, Switzerland
[22] Filed: Sept. 11, 1975
[21] Appl. No.: 612,555
[30] Foreign Application Priority Data
Sept. 17, 1974 Switzerland .................... 12593/74
[52] U.S. Cl. .............................. 210/180; 210/186; 210/416 M; 210/436; 210/DIG. 23
[51] Int. Cl.² ......................................... B01D 31/00
[58] Field of Search .......... 210/416, 435, 436, 453, 210/489, 180, 186, DIG. 23

[56] References Cited
UNITED STATES PATENTS

| | | |
|---|---|---|
| 2,990,238 | 6/1961 | Kabisch et al. .................... 210/416 |
| 3,541,004 | 11/1970 | Cooper et al. ....................... 210/19 |
| 3,567,031 | 3/1971 | Loeffler ............................. 210/416 |
| 3,844,895 | 10/1974 | Rose et al. ......................... 210/436 |

Primary Examiner—Bernard Nozick
Attorney, Agent, or Firm—Oblon, Fisher, Spivak, McClelland & Maier

[57] ABSTRACT

An apparatus for sieve filtration, and in particular ultrafiltration using a membrane as the filter, is particularly useful for filtering extremely small initial volumes, in particular of blood plasma or serum, in a pressurized cell with alternating flow direction of the liquid to be filtered, thus preventing concentration polarization, and preventing contact of the liquid to be filtered with any foreign substance such as a pressure gas.

9 Claims, 5 Drawing Figures

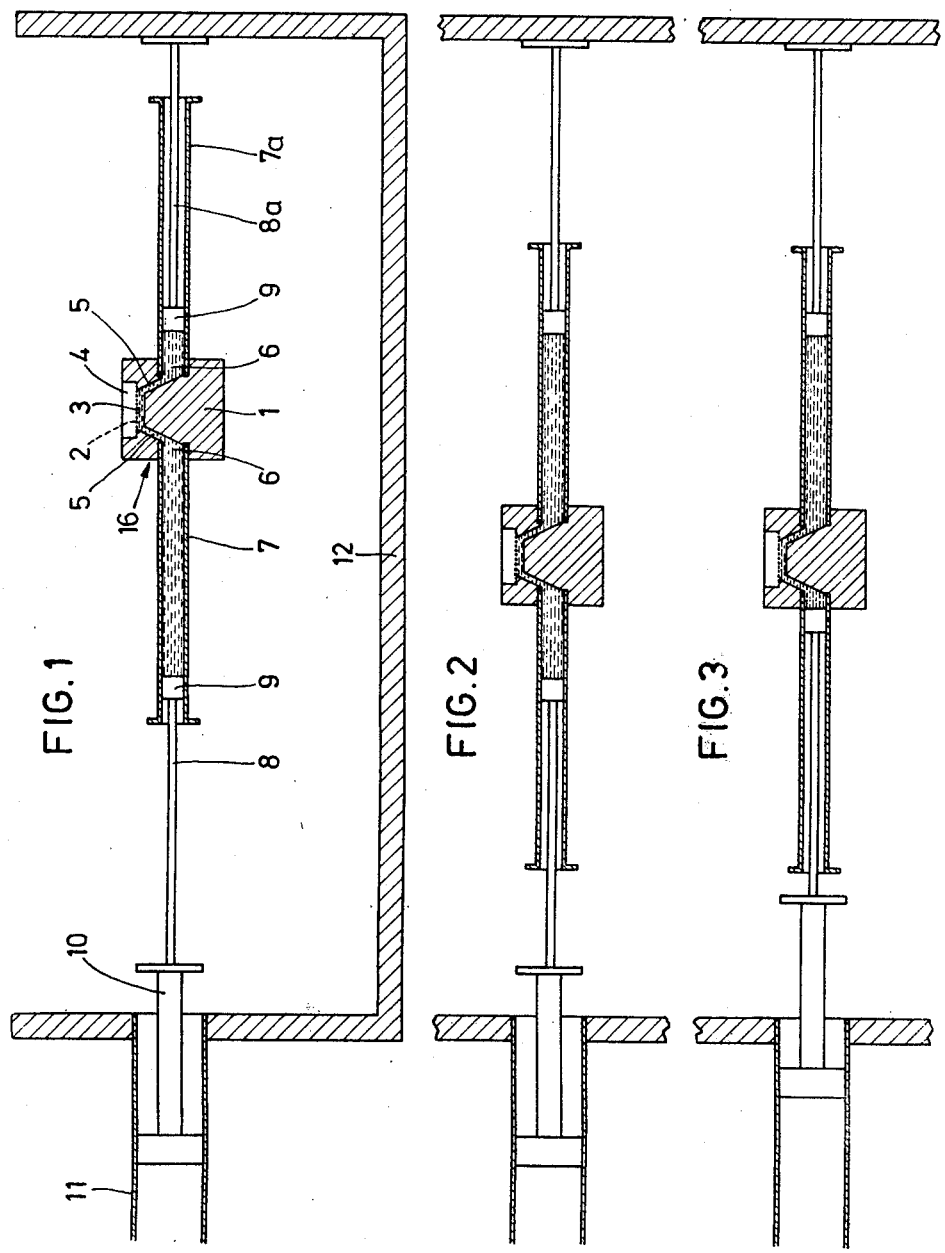

SIEVE FILTRATION APPARATUS

This invention relates to a sieve filtration apparatus comprising at least one filtering vessel having an inlet side and an outlet side and at least one sieving filter dividing each filtering vessel into a primary chamber on the inlet side and a secondary chamber on the outlet side. The invention particularly relates to the use of the apparatus for ultrafiltration.

Sieve filtration, which also comprises membrane filtration or ultrafiltration, differs from other filtering processes in that the separated particles are deposited on the visible surface of a thin-layer filter medium, that is the sieving filter, so that solely particles which are larger than the apertures in the particular sieving filter can be separated by sieve filtration. As the layer of deposited particles becomes thicker, the filtering efficiency decreases, and the filtration characteristics may also be altered by the filter cake being produced. Hence the practical significance of sieve filtration resides primarily in the separation of relatively coarse-grained solid particles which can be prevented from accumulating on the surface of the sieving filter by holding the latter at an angle and shaking it.

The separation of extremely fine particles, including those so small as to be molecular in size, entails the risk of clogging the pores of the sieving filter. Since it as become possible to produce filter membranes having pore sizes of from 10 microns down to 0.002 microns, the effective separation of such fine particles makes it indispensable to prevent the deposition of the particles on the surface of the membrane and its resultant clogging. Another possibility of increasing the yield in membrane filtration is the application of pressure.

Ultrafiltration or membrane filtration has become increasingly important in recent years, e.g., for concentration by the separation of water or aqueous solutions without phase change, concentration of substances in solution or in suspension; desalination by rapid separation of smaller molecules or salts, or buffer interchange; purification by separation of molecules of either high or low molecular weight; and fractionating by separating mixtures into components having differing molecular weights or separation of free substances from macromolecule-bound substances.

For such filtration, various methods and apparatus are known which operate using filter membranes, with or without the application of pressure on the liquid to be filtered, and in which the separated particles are prevented from accumulating on the membrane surface by stirring, vibration, or flux of the liquid to be filtered across the membrane surface.

Various methods are in current use for ultrafiltration of blood plasma or blood serum, e.g., the centrifugation method without excess pressure, where the filtration pressure is obtained by centrifugation. In this method, either filler membranes such as that sold under the trade designation "Centriflo" by Amicon Corporation, Lexington, Mass., or that sold under the trade designation "Pellicon" by Millipore Corporation, Bedford, Mass., are used, or the plasma is centrifuged in a dialysis tube. These methods are easy to carry out from a technical standpoint, and hence and relatively inexpensive, and they make it possible to carry out several filtration operations simultaneously. However, such methods also have certain drawbacks, e.g., for one thing, the relatively large filter surface, which encourages the accumulation of macromolecules, and for another, the need for a relatively large initial volume of preferably 3-5 ml., and at least 1-2 ml., of plasma. In the case of ultrafiltration under pressure, the filter membrane is in a pressurized cell, and the filtration pressure is produced by a pressurized gas. As already mentioned, the accumulation of macromolecules on the membrane surface is prevented in one of the following ways: a magnetic stirring rod situated just above the membrane surface, turbulence produced on the membrane surface by vibration, or laminar flow across the membrane surface through circulation of the plasma. These measures prevent the deposition of macromolecules on the membrane surface and provide efficient filtration. However, they require both expensive apparatus and an initial volume of preferably 3 ml. or more, but at least 1 ml., of plasma.

Various problems are encountered in the ultrafiltration of blood plasma or serum. Concentration polarization resulting from the deposition on the membrane surface of non-ultrafilterable substances, chiefly proteins, can be prevented through the use of pressurized cells, as described above, but it cannot be avoided in centrifugation systems.

The ultrafilterability of certain substances is dependent upon the pH. The pH of blood plasma is a function of the carbon dioxide partial pressure, $pCO_2$. In order to prevent pH changes during ultrafiltraton, the $pCO_2$ has to therefore be kept constant. This can be achieved either by ultrafiltration under oil, which enables filtration at the native pH of the anaerobically-recovered plasma and enters into consideration for centrifugation methods, but less so with pressurized cells, or by equilibration of the plasma with a gas mixture of 95% air and 5% $CO_2$ by volume at atmospheric pressure. The $pCO_2$ of 40 mm. Hg of this mixture corresponds approximately to the physiological $pCO_2$ of the plasma, and filtration must then be carried out in an atmosphere having the same $pCO_2$. The same gas mixture may also be used in centrifugation methods, whereas in the case of filtration under pressure, the mixture must be such that the $pCO_2$ is 40 mm. Hg at the operating pressure. The drawback of this method is that filtration cannot be carried out at either the native pH or the standard pH since the pH of the plasma at a given $pCO_2$ is a function of the ($HCO_3^{116}$) content. The $pCO_2$ is easy to control in centrifugation systems but hard to control when pressurized cells are used.

Inasmuch as certain substances are adsorbed on parts on the filtration apparatus, e.g., on the filter membrane, the filter area and the surface of the filter support for use with a small volume of plasma should be as small as possible, yet enable concentration polarization to be prevented.

For analytical purposes, 100–300 $\mu l$ of ultrafiltrate from blood plasma or serum are sufficient. Since it is not expedient to filter out more than 30% of the initial plasma volume, the required initial volume is from 0.4 −1 ml.

Most of the known filtration apparatus are either elaborate and therefore expensive or require relatively large quantities of liquid for their operation. U.S. Pat. No. 3,541,005, for instance, teaches a method in which a laminar flow running parallel to the filter membrane is produced above the membrane for preventing the concentration polarization. This so-called "thin-channel system", as its name implies, requires an elaborate installation for achieving and maintaining the laminar ow by means of thin channels, the filter pressure being produced by a pressure gas, so that the liquid to be filtered is in contact with that gas. Furthermore, for performing this method in the apparatus designed for it, a relatively large volume of liquid is required since the circulation is produced by means of a peristaltic pump.

It is an object of this invention to provide a sieve filtration apparatus which is simple in its construction, offers the possibility of working at various temperatures, allows several filtration operations to be carried out simultaneously in a simple manner, and can, moreover, be used satisfactorily with a very small volume of the liquid to be filtered.

It is a further object of the invention to provide a sieve filtration apparatus suitable for use in ultrafiltration, using a membrane filter as the sieving filter.

To this end, the filtration apparatus according to the present invention further comprises two coaxial cylinders disposed on opposite sides of each filtering vessel, projecting outwardly therefrom, and communicating with the primary chamber, the filtering vessel and the cylinders forming an integral unit, at least two pistons, each having a piston-rod cooperating with a respective cylinder, at least one of the pistons being movable for producing and stabilizing a predetermined pressure in the vessel-cylinder unit, and means for producing a relative reciprocating movement between the vessel-cylinder unit and the pistons parallel to the axis of the cylinders.

Essential advantages of the invented apparatus are that it can be of very simple construction which does not allow for formation of a laminar flow at all, that the liquid to be filtered does not come into contact with any pressure gas, and that it enables the simple and efficient ultrafiltration of such a small volume of liquid as has not heretofore been possible. The relative movement mentioned causes the liquid to be filtered to flow through the filtering vessel, thus preventing concentration polarization. Since there is no gas space above the liquid to be filtered, the $pCO_2$ remains constant. Inasmuch as the filtering vessel is very small, virtually no adsorption phenomena occur. The apparatus makes it possible to work at various temperatures, e.g., in a dry-air incubator or a refrigerator, and it takes up very little space.

Although the invented apparatus may be used for sieve filtration in general, depending upon its capacity and the type of sieving filter used, it is designed primarily for filtration, particularly ultrafiltration, of a small starting volume of the liquid to be filtered, e.g., from 100 $\mu l$ to 10 ml., preferably 0.5 to 1 ml., and especially for ultrafiltration of liquids containing such a large proportion of non-filterable substances or particles that their deposition on the filter surface during filtration may reduce the yield of filtrate and, when a membrane filter is used, may also modify the retention properties thereof by formation of a secondary membrane. The invented apparatus is particularly suitable for ultrafiltration of biological liquids, especially blood plasma or blood serum, using ultrafilter membranes having various molecular cut-off limits, e.g., for molecular weights of 100,000, 50,000, 30,000, 25,000, 15,000, 10,000, 1,000, 500, or others. A further advantage of the invented apparatus is that liquids may be filtered which should not be in direct contact with a gas space during filtration, e.g., liquids which are volatile or contain volatile components, such as liquids containing a buffer having one or more volatile components, especially bicarbonate buffers, for preventing pH changes during filtration.

In a particularly advantageous embodiment of the invention, the primary chamber comprises a closable filling tube and a closable air-vent, and the secondary chamber communicates with a receptacle for the filtrate.

In another preferred embodiment of the invention, a number of vessel-cylinder units are secured in a common holding-frame movable along a track and are set into a chassis. One piston-rod of each individual unit is integral with the wall of the chassis, while the opposite piston-rod of each individual unit is integral with the piston-rod of a pressure-cylinder set associated with each unit. The drive means producing the relative reciprocating movement then acts upon the common frame.

The further advantage of the foregoing embodiment is that several filtrations can be carried out simultaneously.

Figure 5:
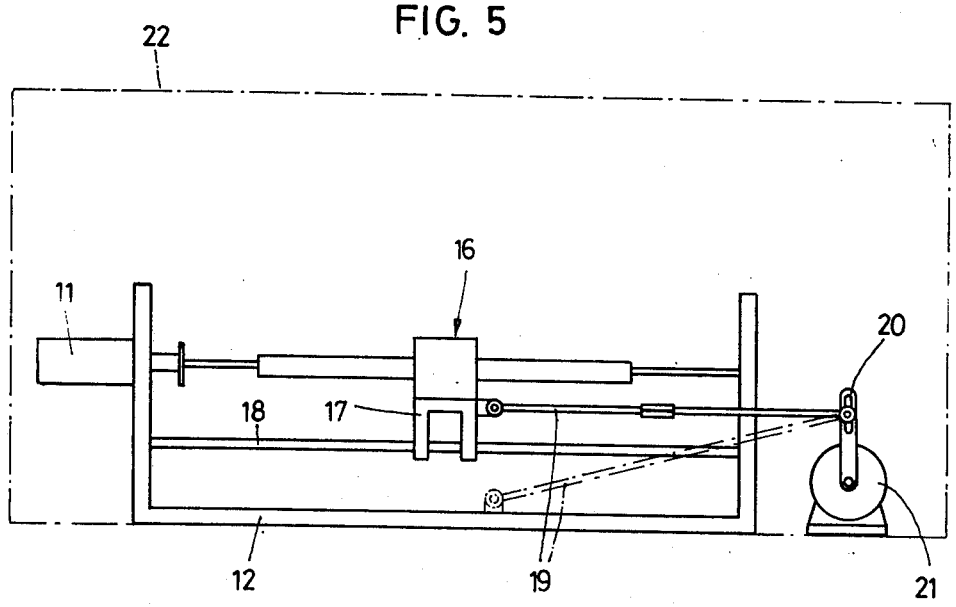

Other objects and advantages of the invention will become apparent from the following detailed description of a preferred embodiment thereof and of a method of using it for the ultrafiltration of blood plasma, taken in conjunction with the accompanying drawings, in which:

FIG. 1 is a sectional diagram of an apparatus intended for the ultrafiltration of an initial volume of 0.5 ml. of liquid, FIGS. 2 and 3 are partial sectional diagrams analogous to FIG. 1, showing the same apparatus in two other stages of movement and omitting the reference numerals for the sake of simplicity, FIG. 4 is a detail view on a larger scale of the part of the apparatus designated generally as 16 in FIG. 1, FIG. 5 is a diagram of means for producing the relative reciprocating movement.

The filtering vessel takes the form of a plastic block 1 divided by a filter membrane 2 (e.g., the membrane sold by Amicon Corporation under the trade designation XM-50), 13 mm. in diameter, into a primary chamber 3 and a secondary chamber 4. Primary chamber 3 is 0.1 mm. high and communicates via two channels 5 with two coaxial bores 6 formed in opposite sides of block 1. Two syringes 7 and 7a are fluid-tightly fitted respectively into each of the bores 6. As shown in FIG. 4, primary chamber 3 also communicates with a closable filling tube 12 and a closable air-vent 13, while secondary chamber 4 communicates with a receptacle 14 for the filtrate. Facing primary chamber 3, filter membrane 2 lies against a frit 15 (e.g., the frit sold by Millipore Corporation under the trade designation "Swinnex") which, on the side toward membrane 2, has a system of notches into which the filtrate penetrates and then flows through holes in frit 15 into secondary chamber 4 and thence into receptacle 14.

Syringes 7 and 7a may be disposable 1-ml. plastic syringes of the type sold by Sherwood Medical Industries, Crawley, Sussex, England, under the trade designation "Brunswick," the plastic plunger-rods of which have been replaced by metal rods 8, 8a to which the original plungers 9 are re-attached, preferably after having been treated with silicone grease. Syringes made of glass, metal, or some other material may also be used. The free end of plunger-rod 8a is integral with one wall of a chassis 12, while the free end of plunger-rod 8 is connected to a piston-rod 10 of a pressure-cylinder set 11 inserted in the opposite wall. The set 11 is a simple-operating type of microcylinder available from Universo S.A., La Chaux-de-Fonds, Switzerland, under the trade designation UVC 10/75 F, having a bore of 10 mm. and a 75-mm. stroke. It is operated by compressed air or some other pressure gas. A hydraulically-operated pressure-cylinder set might also be used, however. The operating pressure is determined by the desired filtration pressure and depends upon the kind of liquid to be filtered and the filter membrane used, in which connection the piston diameter of the syringes employed must also be taken into consideration. When, for example, the aforementioned "Diaflo" XM-50 filter membrane and 1-ml. "Brunswick" syringes are used for ultrafiltration of blood plasma, the operating pressure will be within a range of from 4–6 kg./sq.cm.

The means for producing relative reciprocating movement between the pistons or plungers 9 and the vessel-cylinder unit designated generally as 16 and comprising essentially block 1 and syringes 7 and 7a in the embodiment being described, parallel to the axis of syringes 7 and 7a, may expediently be constructed as follows, as shown in FIG. 5: unit 16 is secured to a holder-frame 17 which is mounted on a track 18 running parallel to syringes 7, 7a in such a way that it can be moved back and forth in line with the longitudinal axis of the two coaxial syringes 7, 7a. Connected to frame 17 is one end of a driving rod 19 which is adjustable in length. The other end of driving rod 19 is connected to an eccentric 20, the radius of which is likewise adjustable. Eccentric 20 is driven by an electric motor 21 with variable speed-control.

Although the foregoing describes a preferred type of reciprocation, it would be quite possible to provide a stationary arrangement of holding-frame 17 and unit 16 as indicated by dot-dash lines in FIG. 5, and to move chassis 12 back and forth instead. The means for driving either unit 16 and frame 17 or chassis 12 back and forth might also be of another kind, e.g., a pneumatic system controlled by stops and reversing valves or an electric system controlled by stops and reversing switches. It is merely necessary to ensure that the center position of unit 16 and the amplitude of the movement be variable at will.

The apparatus may be disposed in a thermostatically-controlled container 22, if so desired.

The mode of operation of the described embodiment of the invented apparatus for ultrafiltration of blood plasma will now be explained.

Plungers 9 of the two syringes 7 and 7a are pushed all the way into the bodies thereof on both sides so that the air space in unit 16 is minimal. A quantity of 0.5 ml. of plasma is injected into primary chamber 3 of block 1 through filling tube 12, which is then closed off by means of a shut-off cock. Primary chamber 3 is vented through air-vent 13. Next the operating pressure in unit 16 is set to the predetermined value by means of pressure-cylinder set 11. Before the drive is switched on, the center position and amplitude of the movement must be adapted to the volume of the liquid, the center position being set by adjusting the length of driving rod 19 and the amplitude by adjusting the radius of eccentric 20. At dead center of the movement toward syringe 7a, the latter should be empty before the drive is started up. At dead center of the opposite movement, syringe 7 should, when filtration begins, contain a volume of plasma corresponding to the desired volume of ultrafiltrate, so that when filtration is terminated, syringe 7 is empty at this dead center position. In ultrafiltration of blood plasma, the volume of the ultrafiltrate should not exceed 30% of the initial volume of the plasma. The rhythm of the relative movement is adapted to the kind of liquid to be filtered. For the ultrafiltration of blood plasma, the movement should be slow.

When ultrafiltration has been completed, the drive is switched off, the ultrafiltrate is pipetted off from receptacle 14, and unit 16 is emptied through tube 12. The apparatus may be cleaned either by repeating the operation as described above a number of times with distilled water or by dismantling the apparatus and cleaning the parts separately.

What is claimed is:

1. A sieve filtration apparatus comprising:
   at least one filtering vessel having an inlet side and an outlet side and at least one sieving filter dividing said at least one vessel into a primary chamber on said inlet side and a secondary chamber on said outlet side,
   two coaxial cylinders disposed on opposite sides of said at least one vessel, projecting outwardly therefrom, and communicating with said primary chamber, said vessel and said cylinders forming an integral unit,
   at least two pistons, each having a piston-rod and cooperating with a respective one of said cylinders, at least one of said pistons being movable for producing and stabilizing a predetermined pressure in said vessel-cylinder unit, and
   means for producing a relative reciprocating movement between said vessel-cylinder unit and said pistons parallel to the axis of said cylinders.

2. A sieve filtration apparatus according to claim 1, wherein said primary chamber comprises a closable filling tube and a closable air-vent.

3. A sieve filtration apparatus according to claim 1, further comprising a filtrate-receptacle communicating with said secondary chamber.

4. A sieve filtration apparatus according to claim 1, further comprising at least one pressure-cylinder set, operated pneumatically or hydraulically and having a piston-rod, said pressure-cylinder piston-rod being connected to one of said piston-rods of one of said pistons cooperating with one of said cylinders for producing and stabilizing said predetermined pressure.

5. A sieve filtration apparatus according to claim 1, wherein said vessel takes the form of a block made of synthetic material, said cylinders consist of syringes, said block comprising bores in opposite walls thereof for receiving said syringes, and said sieving filter is a filter membrane, said apparatus further comprising channels connecting said bores to said primary chamber and a frit disposed in said secondary chamber, said membrane lying against said frit and facing said primary chamber.

6. A sieve filtration apparatus according to claim 5, wherein said syringes each have a capacity of 1 ml.

7. A sieve filtration apparatus according to claim 1, further comprising a frame to which said vessel-cylinder unit is secured and a chassis in which said at least one pressure-cylinder set and one of said piston-rods of one of said pistons cooperating with another one of said cylinders are secured for allowing said relative reciprocating movement by displacement of either one of said frame or said chassis.

8. A sieve filtration apparatus according to claim 7, further comprising a track running parallel to the axis of said cylinders, a driving rod connected at one end to said frame, and an eccentric secured to the other end of said driving rod and adapted to be driven, said frame being movably disposed on said track, said driving rod being adjustable in length, and said eccentric having an adjustable radius.

9. A sieve filtration apparatus according to claim 7, further comprising a thermostatically-controlled container in which said chassis is disposed.

* * * * *